United States Patent
Mazoyer et al.

(10) Patent No.: US 10,994,264 B2
(45) Date of Patent: May 4, 2021

(54) CATALYSTS AND PROCESSES FOR MAKING CATALYSTS FOR PRODUCING NEOPENTANE

(71) Applicant: ExxonMobil Chemical Patents Inc., Baytown, TX (US)

(72) Inventors: Etienne Mazoyer, Woluwe Saint Pierre (BE); Kun Wang, Bridgewater, NJ (US); Helge Jaensch, Grimbergen (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 86 days.

(21) Appl. No.: 16/390,844

(22) Filed: Apr. 22, 2019

(65) Prior Publication Data

US 2019/0366306 A1    Dec. 5, 2019

Related U.S. Application Data

(60) Provisional application No. 62/677,981, filed on May 30, 2018.

(51) Int. Cl.
| | | |
|---|---|---|
| *B01J 23/755* | (2006.01) | |
| *C07C 9/18* | (2006.01) | |
| *C07C 4/10* | (2006.01) | |
| *B01J 37/02* | (2006.01) | |
| *B01J 21/08* | (2006.01) | |

(Continued)

(52) U.S. Cl.
CPC ............ *B01J 23/755* (2013.01); *B01J 21/08* (2013.01); *B01J 37/0207* (2013.01); *B01J 37/035* (2013.01); *B01J 37/08* (2013.01); *B01J 37/18* (2013.01); *C07C 4/10* (2013.01);

(Continued)

(58) Field of Classification Search
CPC . B01J 23/755; B01J 23/40; B01J 23/74; B01J 23/89; B01J 21/08; B01J 37/0207; B01J 37/035; B01J 37/08; B01J 37/18; B01J 21/04; B01J 21/12; B01J 21/16; C07C 4/10; C07C 9/14; C07C 9/18;

(Continued)

(56) References Cited

U.S. PATENT DOCUMENTS

| | | |
|---|---|---|
| 2,325,052 A | 7/1943 | Grosse et al. |
| 2,394,743 A | 2/1946 | Bergsteinsson |

(Continued)

FOREIGN PATENT DOCUMENTS

| | | | |
|---|---|---|---|
| GB | 574694 | 1/1946 | |
| GB | 873449 A * | 7/1961 | ......... B01J 27/1853 |

(Continued)

OTHER PUBLICATIONS

Vogelzang et al., "Reactions of 2,2-Dimethylbutane on Iridium: The Role of Surface Carbonaceous Layers and Metal Particle Size," Journal of Catalysis, vol. 111, pp. 77-87 (1988).

(Continued)

*Primary Examiner* — Patricia L. Hailey

(57) ABSTRACT

Catalysts and processes for producing catalysts for neopentane production are provided herein. A process includes reducing a catalyst precursor comprising a transition metal and an inorganic support at a temperature less than 500° C. to produce a catalyst. Also provided herein are processes to produce neopentane using the catalysts described herein and neopentane compositions produced therefrom.

24 Claims, 3 Drawing Sheets

(51) Int. Cl.
  *B01J 37/18* (2006.01)
  *B01J 37/03* (2006.01)
  *B01J 37/08* (2006.01)

(52) U.S. Cl.
  CPC ............ *C07C 9/18* (2013.01); *C07C 2521/08* (2013.01); *C07C 2523/755* (2013.01)

(58) Field of Classification Search
  CPC ............ C07C 2521/08; C07C 2523/38; C07C 2523/70; C07C 2523/755
  USPC .................................................. 502/325, 326
  See application file for complete search history.

(56) References Cited

U.S. PATENT DOCUMENTS

| | | | |
|---|---|---|---|
| 2,413,691 A | 1/1947 | Crawford et al. | |
| 2,422,670 A | 6/1947 | Haensel et al. | |
| 2,422,672 A | 6/1947 | Haensel et al. | |
| 2,422,674 A | 6/1947 | Haensel et al. | |
| 2,422,675 A | 6/1947 | Haensel et al. | |
| 2,436,923 A | 3/1948 | Haensel et al. | |
| 2,441,663 A * | 5/1948 | Haensel | 203/32 |
| 2,470,712 A * | 5/1949 | Horne | C07C 4/18 585/401 |
| 2,897,137 A * | 7/1959 | Schwarzenbek | C10G 35/09 208/140 |
| 2,970,954 A * | 2/1961 | Munns, Jr. | C07C 4/10 208/57 |
| 3,047,491 A * | 7/1962 | Carr | C07C 4/10 208/136 |
| 3,564,068 A * | 2/1971 | Kroll | C07C 4/08 585/489 |
| 3,585,252 A | 6/1971 | Kennedy | |
| 3,660,516 A | 5/1972 | Crain et al. | |
| 3,755,493 A | 8/1973 | Norell | |
| 3,855,346 A | 12/1974 | Norel | |
| 4,166,077 A * | 8/1979 | Bernard | C07C 11/04 585/310 |
| 4,593,147 A | 6/1986 | Butter et al. | |
| 4,940,829 A | 7/1990 | Drake | |
| 5,146,037 A | 9/1992 | Zarchy et al. | |
| 6,197,721 B1 * | 3/2001 | Didillon | B01J 23/40 502/326 |
| 6,262,192 B1 | 7/2001 | Wu | |
| 7,067,453 B1 * | 6/2006 | Ming | B01J 23/40 423/652 |
| 2007/0043247 A1 | 2/2007 | Webber et al. | |
| 2014/0374319 A1 * | 12/2014 | Soled | C10G 45/08 208/215 |
| 2019/0169092 A1 * | 6/2019 | Wang | C07C 5/2708 |
| 2019/0177248 A1 * | 6/2019 | Wang | C07C 2/12 |
| 2019/0225561 A1 * | 7/2019 | Wang | C10L 1/04 |
| 2019/0367429 A1 * | 12/2019 | Mazoyer | B01J 23/44 |

FOREIGN PATENT DOCUMENTS

| | | |
|---|---|---|
| GB | 1220105 | 1/1971 |
| WO | 2018/044591 | 3/2018 |
| WO | 2018/044592 | 3/2018 |
| WO | 2018/044596 | 3/2018 |

OTHER PUBLICATIONS

Birkhoff et al., "NExOCTANE™ Technology for Isooctane Production," in Handbook of Petroleum Refining Processes, Third Edition, Ch. 1.1 (2004).

Zimmer, H. et al., "Hydrogenolysis of alkanes with quaternary carbon atoms over Pt and Ni black catalysts", J.Chem. Soc., Fararday Trans. 1, 1982.

Himes et al., "UOP HF Alkylation Technology," in Handbook of Petroleum Refining Processes, Third Edition, ch. 1.2 (2004).

Cusher, "UOP Penex Process," Handbook of Petroleum Refining Processes, Third Edition, Ch. 9.3 (2004).

Matsumoto et al., "The classification of metal catalysts in hydrogenolysis of hexane isomers," Journal of Catalysis, vol. 22, pp. 182-192 (1971).

Paál et al, "On the pattern of hydrogenolysis of hexane isomers over four Group VIIIB metals," Reaction Kinetics and Catalysis Letters, vol. 12(2), pp. 131-137 (1979).

Schepers F.J., "Apparent particle size sensitivity in hydrocarbon reactions," J. Catal. 96, 82-87, 1985.

Richardson J. et al., "Crystallite Size Distributions and Stabilities of Homogeneously Deposited Ni/SiO2 Catalysts," Stu. Surf. Sci. Catal. 3, 131-142, 1979.

Song C. et al., "Properties of the Ni/Kieselguhr catalysts prepared by precipitation method," Korean J. of Chem. Eng. 9 (3) 159-163, 1992.

Zidek, Zdeno et al., "Nickel-silica-alumina catalysts. III. Catalytic properties. Hydrocracking of isooctane", 1969.

Seth et al., "Selective hydrogenation of 1,3-butadiene in mixture with isobutene on a Pd/@a-alumina catalyst in a semi-batch reactor", vol. 62, No. 17.

Avdonina, E.N., "Reactions of tritium recoil atoms in liquid mixtures of isooctane with benzene," XP002768312 & vol. 15, No. 5, 1973, pp. 720-726.

Clarke et al., "The Preparation and Activity for Alkane Reactions of Aerosil-Supported Rhodium-Copper Clusters," Journal of Catalysis, vol. 111, pp. 374-382 (1988).

Haensel et al., "Selective Demethylation of Paraffin Hydrocarbons: Preparation of Triptane and Neopentane," Industrial and Engineering Chemistry, vol. 39, pp. 853-857 (1947).

Foger et al., "Skeletal Reactions of Hydrocarbons over Supported Iridium-Gold Catalysts," Journal of Catalysis, vol. 64, pp. 448-463 (1980).

Machiels, et al., "Hydrogenolysis of 2,2-Dimethylbutane and n-Hexane over Supported Ruthenium, Nickel, Cobalt, and Iron," Journal of Catalysis, vol. 58, pp. 268-275 (1979).

Leclercq et al., "Hydrogenolysis of Saturated Hydrocarbons: Influence of Hydrocarbon Structures on the Activity and Selectivity of Nickel on Silica," Journal of Catalysis, vol. 99, pp. 1-11.

Kranz, K., "Alkylation chemistry-Mechanism, operating variables, and olefin interactions", DuPont Company, 2003.

Graves, "STRATCO Effluent Refrigerated H2SO4 Alkylation Process," in Handbook of Petroleum Refining Processes, Third Edition, ch. 1.2 (2004).

Roeseler, "UOP Alkylene™ Process for Motor Fuel," in Handbook of Petroleum Refining Processes, Third Edition, ch. 1.3 (2004).

Matsumoto et al., "Contrast between nickel and platinum catalysts in hydrogenolysis of saturated hydrocarbons," Journal of Catalysis, vol. 19(2), p. 101 (1970).

Richardson J. et al , "Preparation variables in nickel catalysts", J. Catal. 54, 207-218, 1978.

Mendioroz S. et al., "Effect of the method of preparation on the activity of nickel Kieselguhr catalyst for vegetable oil hydrogenation," Appl. Catal. 66, 73-90, 1990.

Hadley, G.R., "Thermal conductivity of packed metal powders," International Journal of Heat and Mass Transfer 29.6, 909-920, 1986.

Coenen J., "Catalytic hydrogenation of fatty oils," Ind. Eng. Chem. Fundamen. 25 (1) 43-52, 1986.

Ponec et al., "Reaction of hexane isomers on Ni-Copper alloys," Proceedings of the Fifth International Congress on Catalysis, p. 645 (1972).

Bergman et al., Fundamentals of Heat and Mass Transfer, John Wiley & Sons.

* cited by examiner

CATALYSTS AND PROCESSES FOR MAKING CATALYSTS FOR PRODUCING NEOPENTANE

CROSS-REFERENCE TO RELATED APPLICATIONS

This application claims the benefit of Provisional Application No. 62/677,981, filed May 30, 2018. In addition, this invention is related to WO 2018/044591, filed Aug. 18, 2017, WO 2018/044592, filed Aug. 18, 2017, and WO 2018/044596, filed Aug. 18, 2017, each of which is incorporated herein by reference.

FIELD OF INVENTION

The present invention relates to processes for making catalysts for producing neopentane, catalysts for producing neopentane, and processes for using those catalysts for producing neopentane.

BACKGROUND OF INVENTION

Neopentane is a unique nonpolar hydrocarbon molecule that has found industrial use in the form of an inert condensing agent for gas-phase reactions. See, for instance, U.S. Pat. No. 6,262,192. Other potential industrial uses for neopentane include use as a heat removal agent, a blowing agent, and a gasoline blend component due to its relatively high octane numbers. For instance, neopentane has a Research Octane Number (RON) of 85.5 and a Motor Octane Number (MON) of 80.2.

Many conventional processes for producing neopentane have proven unsatisfactory for application on a commercial scale. For example, typical existing processes for synthesizing neopentane utilize stoichiometric reactions of t-butyl-chloride and a Grignard reagent, methyl aluminum dichloride, dimethyl aluminum chloride, or trimethyl aluminum. See, for instance, U.S. Pat. No. 3,585,252. Such stoichiometric reactions generate large amounts of metal halides and are difficult to scale up to produce neopentane at commercial quantities. Likewise, though neopentane may be synthesized by hydrogenation of neopentanoic acid under high pressure and at high temperature, e.g., as described in U.S. Pat. No. 4,593,147, such processes are expensive due to the neopentanoic acid feedstock and suffer from a combination of demanding reaction conditions and low selectivity.

Other proposed processes for producing neopentane involve demethylation of higher carbon-number branched paraffins. For example, U.S. Pat. Nos. 4,940,829 and 2,422,675 each relate to the preparation of neopentane via catalytic demethylation of neohexane. However, these higher carbon-number branched paraffins are not readily available in high concentrations suitable as feedstock that could be utilized on a commercial scale.

Alternatively, a process for producing neopentane by hydrogenating an isobutylene polymer and selectively cracking the hydrogenation product is described in U.S. Pat. No. 2,394,743. However, in addition to producing neopentane, this process also produces large amounts of heavier hydrocarbon components.

The production of neopentane by processes that include the demethylation of higher carbon-number hydrocarbons have recently be disclosed in related applications. For instance, WO 2018/044591 discloses a process that includes dimerizing isobutylene to produce diisobutylene, hydrogenating the diisobutylene to yield isooctane, and demethylating to the isooctane to produce neopentane. Further, WO 2018/044592 discloses a process that includes isomerizing $C_6$ and/or $C_7$ paraffins to produce neohexane and/or neoheptane and demethylating the neohexane and/or neoheptane to produce neopentane. Further still, WO 2018/044596 discloses a process that includes contacting isobutane and butylene under alkylation conditions to produce isooctane and demethylating the isooctane to produce neopentane. Each of these processes is reliant upon a suitable catalyst for the demethylation of the higher carbon-number hydrocarbons to produce the neopentane.

Thus, there is a need for improved catalysts for demethylating higher carbon-number alkanes to produce neopentane. Such catalysts could economically produce neopentane in commercial quantities.

Other references of interest include: "The Preparation and Activity for Alkane Reactions of Aerosil-Supported Rhodium-Copper Clusters," Clarke et al., 111 *Journal of Catalysis*, 374-82 (1988); "Selective Demethylation of Paraffin Hydrocarbons: Preparation of Triptane and Neopentane," Haensel et al., 39 *Industrial and Engineering Chemistry*, 853-57 (1947); "Skeletal Reactions of Hydrocarbons over Supported Iridium-Gold Catalysts," Foger et al., 64 *Journal of Catalysis*, 448-63 (1980); "Reactions of 2,2-Dimethylbutane on Iridium: The Role of Surface Carbonaceous Layers and Metal Particle Size," Vogelzang et al., 111 *Journal of Catalysis*, 77-87 (1988); "Hydrogenolysis of 2,2-Dimethylbutane and n-Hexane over Supported Ruthenium, Nickel, Cobalt, and Iron," Machiels et al., 58 *Journal of Catalysis*, 268-75 (1979); "Hydrogenolysis of Saturated Hydrocarbons: Influence of Hydrocarbon Structures on the Activity and Selectivity of Nickel on Silica," Leclercq et al., 99 *Journal of Catalysis*, 1-11; GB 574694; U.S. Pat. Nos. 2,422,670; 2,436,923; "STRATCO Effluent Refrigerated $H_2SO_4$ Alkylation Process," in Handbook of Petroleum Refining Processes, Third Edition, Graves, ch. 1.2 (2004); "UOP Alkylene™ Process for Motor Fuel," in Handbook of Petroleum Refining Processes, Third Edition, Roeseler, ch. 1.3 (2004); and "UOP HF Alkylation Technology," in Handbook of Petroleum Refining Processes, Third Edition, Himes et al., ch. 1.2 (2004); "Contrast between nickel and platinum catalysts in hydrogenolysis of saturated hydrocarbons," Matsumoto et al., 19(2) *Journal of Catalysis*, 101 (1970); "The classification of metal catalysts in hydrogenolysis of hexane isomers," Matsumoto et al., 22 *Journal of Catalysis*, 182-192 (1971); "Reaction of hexane isomers on Ni-Copper alloys," Ponec et al., *Proceedings of the Fifth International Congress on Catalysis*, 645 (1972); and "On the pattern of hydrogenolysis of hexane isomers over four Group VIIIB metals," Paál et al, 12(2) *Reaction Kinetics and Catalysis Letters*, 131-37 (1979).

SUMMARY OF THE INVENTION

The present invention relates to novel processes for producing catalysts for making neopentane that address the need for catalysts capable of commercially producing neopentane, for example, at high yield, mild reaction conditions, and utilizing readily available feedstock. In one aspect, the present invention relates to a process for producing a catalyst for producing neopentane, the process comprises (or consists of, or consists essentially of) reducing a catalyst precursor that comprises a transition metal and an inorganic support at a temperature less than 500° C. to produce the catalyst. Typically, the catalyst precursor is reduced at a temperature less than 450° C., or preferably, from 375° C. to 425° C. Also, the catalyst precursor can be reduced in the presence of 100 to 500 standard cubic centimeters per minute of hydrogen, preferably, in the presence of 400 standard cubic centimeters per minute of hydrogen.

In another aspect, the present invention relates to a catalyst produced by the processes described herein, for example, by reducing a catalyst precursor comprising (or consisting of, or consisting essentially of) a transition metal and an inorganic support at a temperature less than 500° C. to produce the catalyst. Typically, the catalyst exhibits a relatively high dispersion of the transition metal. For example, in aspects where the transition metal includes nickel, the relatively high dispersion of the transition metal can be indicated by an adsorption of hydrogen gas of at least $0.03H_2$:Ni.

In another aspect, the present invention relates to a process for producing neopentane comprising (or consisting of, or consisting essentially of) reducing a catalyst precursor at a temperature less than 500° C. to produce the catalyst and contacting a stream including $C_6$-$C_8$ alkanes with the catalyst to produce a demethylation product including at least 10 wt % neopentane based on the weight of the demethylation product.

DETAILED DESCRIPTION OF THE EMBODIMENTS

Definitions

Figure 1A:
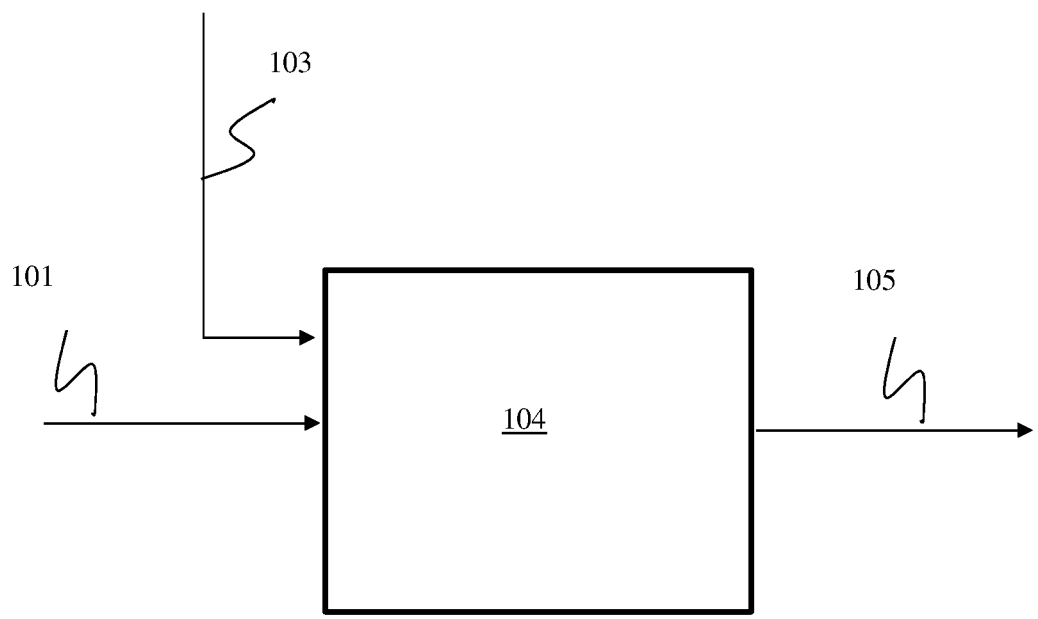
FIG. 1A is a diagram of an example process of producing a catalyst as described herein.

As used herein, the indefinite article "a" or "an" shall mean "at least one" unless specified to the contrary or the context clearly indicates otherwise. Thus, for example, embodiments using "a fractionation column" include embodiments where one, two or more fractionation columns are used, unless specified to the contrary or the context clearly indicates that only one fractionation column is used. Likewise, "a $C_{12}$+ component" should be interpreted to include one, two or more $C_{12}$+ components unless specified or indicated by the context to mean only one specific $C_{12}$+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the subject composition. Thus, for example, the concentrations of the various components of a stream are expressed based on the total weight of that stream. All ranges expressed herein should include both end points as two specific embodiments unless specified or indicated to the contrary.

As used herein, "sccm" means standard cubic centimeters per minute, which is a flow measurement used to indicate the cubic centimeters ($cm^3$) of a gas at standard temperature and pressure passing a given point within one minute. Standard temperature and pressure (STP) refers to a temperature of 273.15 K (0° C.) and an absolute pressure of exactly $10^5$ Pa (100 kPa, 1 bar).

As used herein, the term "catalyst" means a compound capable of initiating catalysis and/or of facilitating a chemical reaction with little or no poisoning/consumption. As used herein, the terms "catalyst precursor" and "pre-catalyst" mean a compound or combination of compounds that, upon being activated, will be capable of initiating catalysis and/or of facilitating a chemical reaction with little or no poisoning/consumption.

As used herein, the term "dispersion" means the ratio of surface-exposed transition metal atoms in comparison to the total number of transition metal atoms. The dispersion of the transition metal ($D_M$) can be calculated as the fraction of surface-exposed atoms of the transition metal ($N_{MX}$) over total number of atoms of the transition metal ($N_{MT}$):

$$DM=N_{MX}/N_{MT}.$$

Typically, $N_{MX}$ and $N_{MT}$ are reported per gram of catalyst. In some aspects, dispersion of the transition metal may be determined experimentally. For example, the dispersion of the transition metal can be determined from the amount of an adsorbate (e.g., $H_2$, CO, $O_2$, $N_2O$) that is adsorbed by the catalyst.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6$^{th}$ Edition, by F. Albert Cotton et al. (John Wiley & Sons, Inc., 1999).

As used herein, "hydrocarbon" refers to molecules or segments of molecules containing primarily hydrogen and carbon atoms. As used herein, the term "$C_n$" hydrocarbon wherein n is a positive integer, e.g., 1, 2, 3, 4, etc., means a hydrocarbon having n number of carbon atom(s) per molecule. The term "$C_n$+" hydrocarbon wherein n is a positive integer, e.g., 1, 2, 3, 4, etc., as used herein, means a hydrocarbon having at least n number of carbon atom(s) per molecule. The term "$C_n$-" hydrocarbon wherein n is a positive integer, e.g., 1, 2, 3, 4, etc., used herein, means a hydrocarbon having no more than n number of carbon atom(s) per molecule.

As used herein, "olefin" refers to any unsaturated hydrocarbon having the formula $C_nH_{2n}$ and containing one carbon-carbon double bond, wherein C is a carbon atom, H is a hydrogen atom, and n is the number of carbon atoms in the olefin.

As used herein, "alkane" or "paraffin" refers to any saturated hydrocarbon having the formula $C_nH_{2n+2}$, wherein C is a carbon atom, H is a hydrogen atom, and n is the number of carbon atoms in the alkane.

As used herein, a "primary carbon atom" refers to a carbon atom neighboring one carbon atom, "secondary carbon atom" refers to a carbon atom neighboring two carbon atoms, "tertiary carbon atom" refers to a carbon atom neighboring three carbon atoms, and "quaternary carbon atom" refers to a carbon atom neighboring four carbon atoms.

As used herein, the prefix "normal" or "n-" signifies a linear unbranched hydrocarbon.

As used herein, the prefix "iso" or "i-" signifies a hydrocarbon containing a methyl substitution at the second carbon of the hydrocarbon chain.

As used herein, the prefix "neo" signifies a hydrocarbon containing a quaternary carbon atom. For example, the term "neopentane" refers to a compound of the formula $C_5H_{12}$ and containing a quaternary carbon atom, otherwise known as 2,2-dimethylpropane.

"Catalyst productivity" is a measure of how many grams of polymer (P) are produced using a polymerization catalyst comprising W g of catalyst (cat), over a period of time of T hours; and may be expressed by the following formula: P/(T×W) and expressed in units of gPgcat$^{-1}$ hr$^{-1}$. Conversion is the amount of monomer that is converted to polymer product, and is reported as mol % and is calculated based on the polymer yield and the amount of monomer fed into the reactor. Catalyst activity is a measure of how active the catalyst is and is reported herein in terms of grams of polymer per millimole of catalyst per hour.

Preparing the Catalyst Precursors

Catalyst precursors described herein comprise a transition metal and an inorganic support. In any embodiment, a catalyst precursor can be prepared by dispersing a transition metal on an inorganic support. Non-limiting examples of suitable transition metals include Group 8, Group 9, and Group 10 transition metals, such as Fe, Co, Ni, Ru, Rh, Pd, Os, Ir, Pt, and combinations thereof, compounds thereof, and mixtures of compounds thereof. In particular embodiments, the transition metal comprises Ni. The transition metal can be present as a single component or, alternatively, can be combined with additional metal(s) to form a binary or ternary alloy. Non-limiting examples of suitable additional metals include Cu, Au, Ag, Sn, Zn, Re, combinations thereof, compounds thereof, and mixtures of compounds thereof.

Additionally, in any embodiment, an inorganic support in a catalyst precursor described herein can be relatively inert with respect to the demethylation reaction. Generally, the inorganic support can comprise or be a porous material, for example, talc, a zeolite, a clay, an organically modified clay, an inorganic oxide, or any other inorganic support material, or mixtures thereof.

In any embodiment, an inorganic support described herein can comprise or be an inorganic oxide in a finely divided form. Non-limiting suitable inorganic oxides for use herein can include metal oxides of groups 2, 4, 13, and/or 14, such as silica, silicates, aluminosilicates, alumina, aluminates, and mixtures thereof. Other inorganic oxides that may be employed either alone or in combination with the silicon/aluminum oxides include those of magnesium, titanium, zirconium, calcium, vanadium, yttrium, niobium, cobalt, nickel, zinc, a lanthanide, or the like, or a combination thereof. Particularly useful inorganic supports include magnesia, titania, zirconia, montmorillonite, phyllosilicate, zeolites, talc, clays, and the like, as well as combinations thereof. Also, combinations of these support materials may be used, for example, silica-chromia, silica-alumina, silica-titania, and the like. Preferred inorganic supports can include silica, alumina, zirconia, and combinations thereof, such as combinations including silica and/or alumina.

In any embodiment, an inorganic support described herein can have a surface area in the range of 10 m$^2$/g to 700 m$^2$/g, or 50 m$^2$/g to 500 m$^2$/g, or 100 m$^2$/g to 400 m$^2$/g. Additionally or alternatively, the inorganic support can have a pore volume in the range of 0.1 mL/g to 4.0 mL/g, or 0.5 mL/g to 3.5 mL/g, or 0.8 mL/g to 3.0 mL/g. The average pore size of the inorganic support can be in the range of 10 Å to 1000 Å, e.g., 50 Å to 500 Å or 75 Å to 350 Å. Additionally or alternatively, the inorganic support can have an average particle size in the range of 5 µm to 500 µm, or 10 µm to 200 µm, or 5 µm to 100 µm. Alternatively, larger particle sizes may also be used. For example, in any embodiment, the inorganic support may have a particle size up to 20 mm. In further embodiments, the inorganic support can have a high surface area, for example, exhibiting a surface area of 200 m$^2$/g to 400 m$^2$/g and a pore volume from 1.2 mL/g to 3.0 mL/gram. An example of an inorganic support having a high surface area is amorphous silica. Non-limiting examples of suitable materials for use as an inorganic support can include or be a silica marketed under the tradename "Davisil™ 646" available from the Davison Chemical Division of W.R. Grace and Company and silicas marketed under the tradename "Aerosil™" available from EVONIK Industries, such as Aerosil™ 200.

In any embodiment, the inorganic support can be dry, that is, substantially free of absorbed water. For example, the inorganic support can be dried by heating or calcining at 100° C. to 1,000° C., or at least 600° C. When the inorganic support comprises silica, the inorganic support can be heated to at least 200° C., for example, 200° C. to 850° C., or 600° C. to 700° C. The inorganic support can be dried for a duration suitable to drive off any adsorbed water, for example, from 1 minute to 100 hours, or from 12 hours to 72 hours, or from 24 hours to 60 hours.

The catalyst precursor can be prepared by any suitable methodology. Suitable methodologies for catalyst precursor preparation are discussed in "Manual of methods and procedures for catalyst characterization," by Haber et al., 67 (8/9) *Pure & Applied Chemistry*, 1257-1306 (1995).

For example, in any embodiment, making the catalyst precursor comprises impregnating an inorganic support, as described herein, with one or more transition metals (e.g., nickel), as described herein. In any embodiment, a transition metal-containing compound (e.g., a nickel-containing compound) can be dissolved in a suitable solvent (e.g., water) to form a solution comprising the transition metal. Non-limiting examples of suitable transition metal-containing compounds can include nickel(II) nitrate, nickel(II) sulfate, nickel(II) chloride, nickel(II) bicarbonate, a nickel(II) carboxylate, palladium(II) chloride, palladium(IV) chloride, palladium(II) nitrate, palladium(II) carboxylate, cobalt(II) nitrate, cobalt(II) nitrate, cobalt(II) chloride, cobalt(II) bicarbonate, cobalt(II) carboxylate, and combinations thereof. In any embodiment, the solution comprising the transition metal can be added to the inorganic support.

Additionally or alternatively, making the catalyst precursor can comprise precipitating the catalyst precursor from a solution including one or more transition metals as described herein and an inorganic support as described herein. Generally, the catalyst precursor can be precipitated from the solution with a precipitating agent, an example of which includes urea. Typically, the solution can be heated and agitated over a suitable duration, for example, during the precipitation.

In any embodiment, methods of making the catalyst precursors described herein can further include shaping the support or the catalyst. The shaping of catalysts and supports can be a key step in a catalyst preparation procedure, particularly for scale-up operations. Extrusion is a common technique which can be used to shape supports and catalysts, such as by screw extrusion. Special shapes can be formed using proper dies. Additionally, in any embodiment, a binder may be added to a support/catalyst, for example, to strengthen the extrudates. Typically, inorganic binders, such as alumina, silica sols, or clays may be used.

In any embodiment, methods of making the catalyst precursors described herein can further include drying the catalyst precursor. The catalyst precursor can be dried by heating or calcining at 100° C. to 1,000° C., or 200° C. to 800° C., or 300° C. to 700° C. The catalyst precursor can be dried for a duration suitable to drive off any adsorbed solvent (e.g., water), for example, from 1 minute to 100 hours, or from 12 hours to 72 hours, or from 24 hours to 60 hours.

Activating the Catalyst Precursors

The catalyst precursors described herein can be activated to produce a catalyst, such as a demethylation catalyst. In any embodiment, a catalyst precursor can be activated by reducing the catalyst precursor. Typically, reducing the catalyst precursor includes heating the catalyst precursor in a reducing environment for a suitable duration. In some aspects, the catalyst precursor is heated at less than 500° C., or from 300° C. to 475° C., or from 350° C. to 450° C., or from 375° C. to 400° C., or from 400° C. to 425° C. Typically, the reducing environment includes a reducing agent (e.g., a reducing gas, such as hydrogen or carbon monoxide). In any embodiment, hydrogen gas ($H_2$) can be the reducing agent and provided to the reducing environment at a rate of at least 100 sccm, or at least 150 sccm, or at least 200 sccm, or at least 250 sccm, or at least 300 sccm, or at least 350 sccm, or at least 400 sccm, or from 100 sccm to 600 sccm, or from 100 sccm to 500 sccm. In any embodiment, the catalyst precursor can be heated in the reducing environment for at least 30 minutes, or at least 1 hour, or from 2 hours to 12 hours, or from 4 hours to 8 hours. Generally, oxidizing agents (e.g., an oxidizing gas such as oxygen) will be absent or substantially absent from the reducing environment.

Not intending to be bound by theory, reduction of the catalyst precursor may be effective to convert the transition metal (e.g., nickel) dispersed on the inorganic support to a more catalytically-active form. Typically, the transition metal is converted from a metal compound to the metallic form.

In any embodiment, catalysts prepared according to the disclosed processes can be characterized as exhibiting a relatively high dispersion of the transition metal in comparison to a similar catalyst produced according to another method. For example, in embodiments where the transition metal includes nickel, the catalyst can exhibit an adsorption of hydrogen gas of at least $0.025H_2$:Ni (mole/mole), or at least $0.03H_2$:Ni, or at least $0.035H_2$:Ni, or at least $0.04H_2$:Ni, or at least $0.045H_2$:Ni, or at least $0.05H_2$:Ni, or at least $0.055H_2$:Ni, or at least $0.06H_2$:Ni. The moles of $H_2$ adsorbed per mole of metal atoms can be determined by a hydrogen chemisorption technique. The hydrogen chemisorption testing can be performed on Micromeritics ASAP 2020 instruments. The following procedure can be followed: Samples can be pretreated under an inert atmosphere such as argon or helium at 250° C. (ramped at 10° C./min from room temperature) for an hour. Then the sample is exposed to hydrogen at 250° C. for one hour to reduce the metal species to its metallic form. The chamber is then evacuated for one hour at 250° C. Under evacuation, the sample is cooled down to 35° C. (20° C./min) and held for five minutes. After a leak test, $H_2$ adsorption is measured at 35° C. During the measurement, the sample is exposed to a series of $H_2$ gas pressures ranging from 1 mmHg to atmospheric pressure; and the amount of hydrogen adsorbed is considered the total $H_2$ adsorption. After the total adsorption isotherm is completed, the sample is evacuated again to remove the weakly adsorbed $H_2$; then the $H_2$ adsorption isotherm measurement is repeated at 35° C. to obtain the amount of weak adsorption. The strong, irreversible adsorption is obtained by subtracting the weak adsorption from the total adsorption. The ranges for $H_2$ adsorption disclosed above are for strong, irreversible adsorption.

Additionally, preferably the acidity of the catalyst is minimized to inhibit undesired cracking reactions when the catalyst is employed in a demethylation reaction, as will be disclosed herein. In any embodiment, the acidity of the catalyst can be reduced via impregnation with an alkali metal compound, for example, an alkali metal hydroxide, nitrate, carbonate, bicarbonate, or oxide, such as sodium oxide ($Na_2O$). In such aspects, the amount of the alkali metal compound present in the catalyst can be from 0.05 wt % to 1.0 wt %, such as from 0.1 wt % to 0.5 wt %, of the total weight of the catalyst.

Demethylation of $C_6$-$C_8$ Alkanes

The catalysts, produced by the methods described herein, can be used to demethylate a $C_6$+ hydrocarbon, for example, a $C_6$-$C_8$ alkane such as neohexane (2,2-dimethylbutane), neoheptane (2,2-dimethylpentane), or isooctane (2,2,4-trimethylpentane). Generally, demethylation is conducted by contacting a stream comprising the $C_6$-$C_8$ alkane with hydrogen in the presence of the catalyst.

The neohexane, neoheptane, and/or isooctane can be derived from any suitable source. For example, isobutylene can be dimerized to produce diisobutylene and the diisobutylene is hydrogenated to yield isooctane, as disclosed in WO 2018/044591:

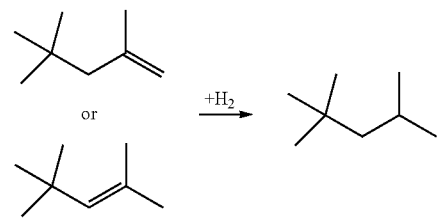

Additionally or alternatively, $C_6$ and/or $C_7$ paraffins can isomerize to produce neohexane and/or neoheptane, as disclosed in WO 2018/044592. Additionally or alternatively, isobutane and butylene can be contacted under alkylation conditions to produce isooctane, as disclosed in WO 2018/044596.

The reaction pathway for the conversion of the $C_6$-$C_8$ alkanes to neopentane typically proceeds by a step-wise demethylation from isooctane to neoheptane, from neoheptane to neohexane, and from neohexane to neopentane, as summarized in the following reaction schemes:

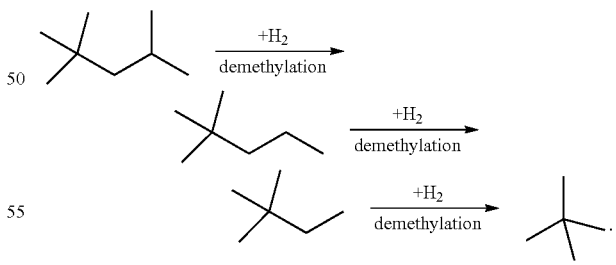

As shown from the reaction scheme above, the desired demethylation occurs at the tertiary (3°) carbon of the isooctane and the secondary (2°) carbon of the intermediates. Competing demethylation reactions can occur at the quaternary (4°) carbon. Advantageously, a catalyst described herein is effective to minimize demethylation at the quaternary (4°) carbon to prevent a loss of neopentane yield.

The catalysts prepared according to the disclosed processes can be characterized as exhibiting improved rates for the conversion of $C_6$-$C_8$ alkanes in comparison to a similar catalyst produced according to another method. In any embodiment, catalysts described herein can be characterized as exhibiting a conversion rate of $C_6$-$C_8$ alkanes of at least 60%, or at least 65%, or at least 70%, or at least 75%, or at least 80%, or at least 85%. For example, a $C_6$ alkane feed can exhibit a conversion rate of greater than 80%, or greater than 90%, or greater than 95%, or greater than 99%, such as 80% to 99%, or 85% to 95%.

Additionally or alternatively, the catalysts prepared according to the disclosed processes can be characterized as exhibiting no loss of selectivity or as exhibiting substantially little loss of selectivity for the production of neopentane while also exhibiting improved rates for the conversion of $C_6$-$C_8$ alkanes to neopentane.

Additionally or alternatively, the catalysts prepared according to the disclosed processes can be characterized as exhibiting improved productivity in the demethylation of $C_6$-$C_8$ alkanes to produce neopentane in comparison to a similar catalyst produced according to another method. For example, in embodiments where the catalyst includes nickel as the transition metal, the catalyst can be characterized as exhibiting a productivity of at least 650 mg·$g_{Ni}^{-1}$·$h^{-1}$, or at least 675 mg·$g_{Ni}^{-1}$·$h^{-1}$, or at least 700 mg·$g_{Ni}^{-1}$·$h^{-1}$, or at least 725 mg·$g_{Ni}^{-1}$·$h^{-1}$, or at least 750 mg·$g_{Ni}^{-1}$·$h^{-1}$, or at least 775 mg·$g_{Ni}^{-1}$·$h^{-1}$, or at least 800 mg·$g_{Ni}^{-1}$·$h^{-1}$, or at least 825 mg·$g_{Ni}^{-1}$·$h^{-1}$, or at least 850 mg·$g_{Ni}^{-1}$·$h^{-1}$.

A demethylation reaction as described herein can be conducted in a wide range of reactor configurations including fixed bed (single or in series), slurry reactors, and/or catalytic distillation towers. In addition, the demethylation reaction can be conducted in a single reaction zone or in a plurality of reaction zones.

In any embodiment, demethylating the $C_6$-$C_8$ alkane can be conducted at a temperature of 200° C. to 500° C., or 300° C. to 400° C. and a pressure at 100 kPa absolute to 10000 kPa absolute (e.g., atmospheric to 1500 psia), such as 300 kPa absolute to 8000 kPa absolute, in the presence of the catalyst. Often demethylation can be conducted at a hydrogen partial pressure of 50 kPa absolute to 3500 kPa absolute (e.g., from 7 psia to 500 psia). Typically, demethylation can be conducted at a hydrogen partial pressure of less than 2500 kPa absolute, preferably less than 2200 kPa absolute, and preferably less than 1000 kPa absolute (e.g., preferably less than 350 psia, or preferably less than 150 psia). Additionally or alternatively, demethylation can be conducted at a hydrogen to hydrocarbon molar ratio of 2:5 to 25:1, or 1:2 to 20:1, or 1:1 to 14:1. In further embodiments, demethylation may be conducted under conditions including a temperature from 220° C. to 300° C.; a pressure from 15 psig to 200 psig (e.g., from 205 kPa absolute to 1400 kPa absolute); and a hydrogen to hydrocarbon molar ratio of 1:1 to 14:1; or any combination thereof.

The product of the demethylation step generally comprises neopentane, $C_4$- hydrocarbon components (e.g., methane, ethane, and propane) and, optionally, partially converted $C_6$+ hydrocarbon intermediate components (e.g., neohexane and neoheptane). Preferably, the product of the demethylation step comprises: at least 10 wt %, preferably at least 25 wt %, preferably at least 35 wt %, and ideally at least 50 wt % of neopentane, such as 25 wt % to 50 wt % or 30 wt % to 40 wt %; less than 75 wt %, preferably less than 65 wt %, and preferably less than 50 wt % of $C_4$- hydrocarbon components such as 25 wt % to 75 wt % or 40 wt % to 60 wt %; less than 5 wt %, preferably less than 1 wt %, and ideally less than 0.5 wt % of non-neopentane $C_5$ hydrocarbon components, such as zero wt % to 1 wt %; and less than 10 wt %, preferably less than 5 wt %, preferably less than 1 wt %, and ideally less than 0.5 wt % of partially converted $C_6$+ hydrocarbon components (e.g., $C_6$-$C_7$ hydrocarbons), such as zero wt % to 10 wt %, or zero wt % to 1 wt %, or 0.5 wt % to 1 wt %.

In any embodiment, the light $C_4$- hydrocarbon components and the $C_6$+ hydrocarbon intermediate components can be removed from the demethylation product, for example, by distillation, thereby yielding a purified neopentane product stream. Preferably, the purified neopentane product stream comprises greater than 80 wt % neopentane, or greater than 90 wt % neopentane, or greater than 95 wt % neopentane, or greater than 99 wt % neopentane, such as 80 wt % to 99 wt % neopentane, or 85 wt % to 95 wt % neopentane when starting with a $C_6$ alkane feed. Other feeds may depend upon the process, for example per pass conversion may be limited to 20% with a recycling loop.

Processes

The processes described herein will now be more particularly described with reference to the examples shown in FIG. 1A, FIG. 1B and FIG. 2. The invention is not limited to these aspects, and the following description is not meant to foreclose other aspects within the broader scope of the invention.

Figure 1B:
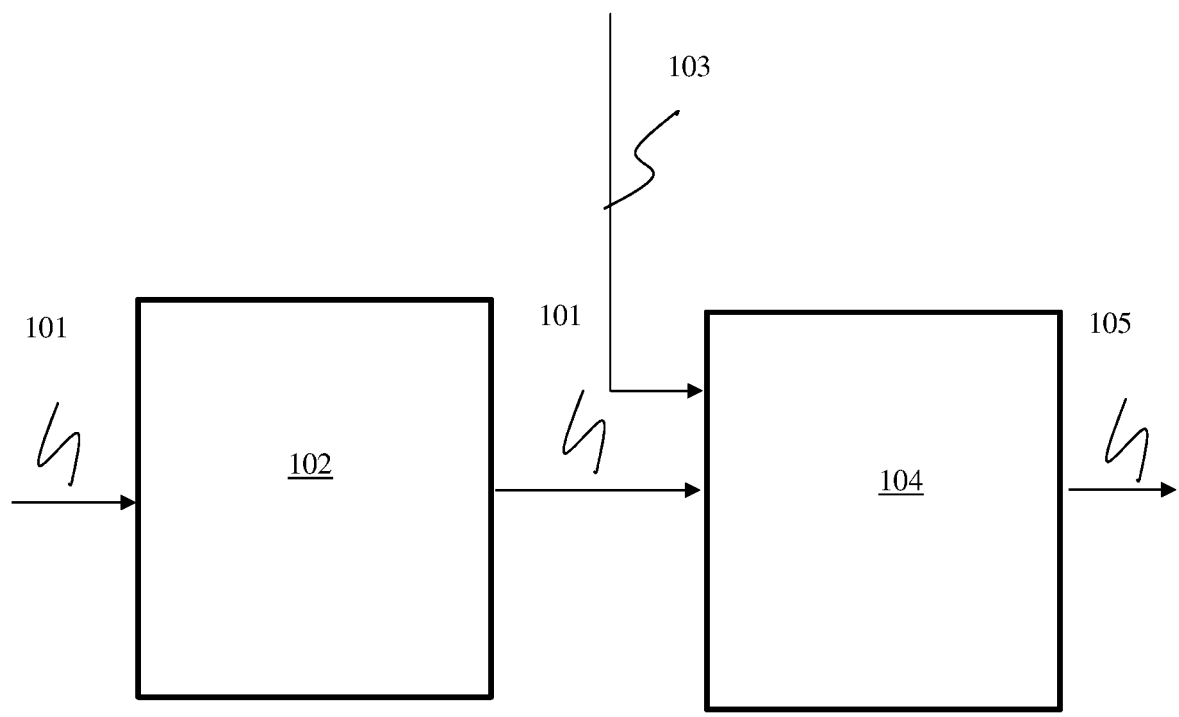
FIG. 1B is another diagram of an example process of producing a catalyst as described herein.

FIG. 1A illustrates an aspect of the disclosed catalyst preparation process, in which a catalyst precursor, including a transition metal and an inorganic support, is reduced at a temperature less than 500° C. to produce the catalyst. The catalyst precursor 101 and a reducing agent stream 103 are fed into a vessel 104. The vessel 104 is maintained at a temperature less than 500° C., preferably from 300° C. to 475° C., preferably 350° C. to 450° C. The catalyst precursor 101 can be retained in the vessel 104 for a duration suitable to activate the catalyst precursor 101 and yield the catalyst 105. Additionally, as shown in FIG. 1B, the catalyst precursor 101 can be optionally dried (e.g., calcined) in a dryer 102 for a suitable duration to drive off any absorbed solvent before entering the vessel 104.

Figure 2:
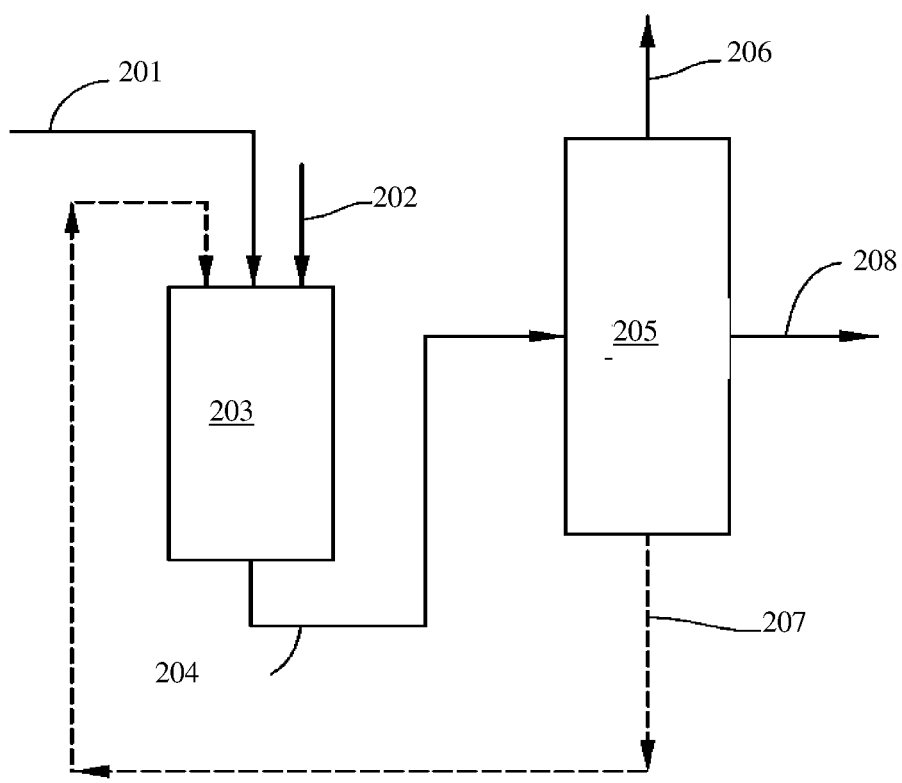
FIG. 2 is a diagram of an example process of producing neopentane as described herein.

FIG. 2 illustrates an aspect of the disclosed neopentane production process, in which a $C_6$-$C_8$ alkane is demethylated to yield the neopentane. As shown in FIG. 2, a feedstream 201 comprising the $C_6$-$C_8$ alkane and a hydrogen stream 202 are introduced to a demethylation reactor 203 to produce a demethylation effluent 204 comprising neopentane, $C_4$- hydrocarbons, and partially converted components, e.g., $C_6$+ hydrocarbons. The demethylation effluent 204 is then fed to a separator 205, for example, a distillation column, to separate a light fraction 206 comprising $C_4$- hydrocarbons and a heavy fraction 207 comprising partially converted $C_6$+ hydrocarbons (primarily, $C_6$-$C_7$ hydrocarbons) from the demethylation effluent 204. The resulting obtained fraction 208 is mainly composed of neopentane. The light fraction 206 can be subjected to further downstream treatment for use as fuel. Optionally, the heavy fraction 207 can be recycled to the demethylation reactor.

In various aspects, neopentane produced in accordance with the present invention is useful as a blowing agent for the production of foamed polymers and possesses several properties (e.g., a boiling point of 9.5° C. and a freezing point of −16.6° C.) making it useful as a heat removal agent and/or an inert condensing agent (ICA) in gas phase polymerization processes, such as for the production of polyethylene. Neopentane produced in accordance with this invention also exhibits high octane numbers and is therefore useful as a gasoline blend component.

The invention will now be more particularly described with reference to the following non-limiting Examples.

EXAMPLES

Example 1: Preparation of 16% Ni/SiO$_2$ Demethylation Catalyst

A 16% Ni/SiO$_2$ catalyst was prepared by impregnation. Silica gel (Davisil™ 646, Sigma-Aldrich) was calcined by heating at a rate of 10° C./min to 700° C. and holding at 700° C. for 15 hours, then cooling to 50° C. and holding at temperature overnight. The pore volume of the calcined silica was determined to be 1.35 mL/g. An aqueous solution of nickel(II) nitrate was prepared by dissolving 42.93 g of nickel(II) nitrate hydrate (Ni(NO$_3$)$_2$·6H$_2$O) in 27 g water. The aqueous solution was added dropwise to 20 g of the calcined silica, to give a Ni loading of 16 wt %. The resultant product was transferred to a ceramic dish, calcined by heating at a rate of 10° C./min to 450° C. and holding for 10 hours, then cooling to 50° C. and holding at temperature overnight.

Example 2: Preparation of 3% Ni/SiO$_2$ Demethylation Catalyst

A 3% Ni/SiO$_2$ catalyst was prepared by impregnation. Silica gel (Davisil™ 646, Sigma-Aldrich) was calcined by heating at a rate of 10° C./min to 700° C. and holding at 700° C. for 15 hours, then cooling to 50° C. and holding at temperature overnight. The pore volume of the calcined silica was determined to be 1.35 mL/g. An aqueous solution of nickel(II) nitrate was prepared by dissolving 4.3 g of nickel(II) nitrate hydrate (Ni(NO$_3$)$_2$·6H$_2$O) in 27 g water. The aqueous solution was added dropwise to 20 g of the calcined silica, to give a Ni loading of 3 wt %. The resultant product was transferred to a ceramic dish, calcined by heating at a rate of 10° C./min to 450° C. and holding for 10 hours, then cooling to 50° C. and holding at temperature overnight.

Example 3: Preparation of 28% Ni/SiO$_2$ Demethylation Catalyst

A 28% Ni/SiO$_2$ catalyst was prepared by precipitation. 87 g of nickel(II) nitrate hydrate (Ni(NO$_3$)$_2$·6H$_2$O), 54 g of urea, and 40 g of Aerosil™ 200 from Evonik Industries were added to 100 mL of water to form a suspension. The suspension was heated at 100° C. with vigorous agitation. After heating for 120 hours, the pH of the suspension was 7.0, indicating that substantially all of the nickel had been precipitated from the suspension. The suspension was filtered and the resulting solid was washed and dried at 120° C. for 20 hours.

Example 4: Preparation of 13% Ni/SiO$_2$ Demethylation Catalyst

A 13% Ni/SiO$_2$ catalyst was prepared by precipitation. 29 g of nickel(II) nitrate hydrate (Ni(NO$_3$)$_2$.6H$_2$O), 18 g of urea, and 40 g of Aerosil™ 200 from Evonik Industries were added to 100 mL of water to form a suspension. The suspension was heated at 100° C. with vigorous agitation. After heating for 120 hours, the pH of the suspension was 7.0, indicating that substantially all of the nickel had been precipitated from the suspension. The suspension was filtered and the resulting solid was washed and dried at 120° C. for 20 hours.

Example 5: Commercial Reference—64% Ni/SiO$_2$ Demethylation Catalyst

A commercial 64% nickel supported on silica catalyst was obtained from STREM Chemicals, Inc. (Newburyport, Mass., United States).

Conversion Testing of Example 1-5 Catalysts

The demethylation catalysts described in Examples 1-5 were activated by reducing each of the catalysts at 400° C. using 500 sccm of H$_2$ for 8 hours at 30 psig. After being reduced, each of the catalysts was characterized with respect to nickel dispersion and was tested for the conversion of isooctane. Each of the catalysts of Examples 1-5 was tested at identical process conditions, including conversion of isooctane at 100 psig, 0.5 h$^{-1}$ WHSV, at 230° C., H$_2$:HC ratio of 14 mol:mol. Based upon the nickel loadings, a productivity number relating the mass of substrate converted for mass of nickel per unit of time was calculated for each catalyst. The results of the characterizations and testing are shown in Table 1:

TABLE 1

Characterization of examples

| Example | Preparation Method | Ni Loading [wt. %] | Adsorption [H$_2$:Ni] | Isooctane Conversion [%] | Productivity [mg · g$_{Ni}^{-1}$ · h$^{-1}$] |
|---|---|---|---|---|---|
| 1 | Impregnation | 16 | 0.01 | 5 | 181 |
| 2 | Impregnation | 3 | 0.01 | 1 | 193 |
| 3 | Precipitation | 28 | 0.04 | 30 | 621 |
| 4 | Precipitation | 13 | 0.03 | 17 | 758 |
| 5 | Reference | 64 | 0.04 | 80 | 725 |

The results of the characterizations and testing of Examples 1-5 show the association between catalysts having relatively high distributions of the transition metal and relatively high conversion rates. Surprisingly, although these catalysts demonstrate improved conversion rates, the catalysts do not demonstrate a loss in selectivity.

Additionally, although the catalysts prepared by impregnation demonstrate relatively low nickel dispersion in comparison to the catalysts prepared by precipitation, impregnation could still be used to produce a catalyst likewise having high dispersion of the transition metal, for example, by optimizing the impregnation process and/or using an organic agent to enhance dispersion.

Examples 6-13

Example 5 catalyst precursor was used for Examples 6-13. The catalyst was activated according to varying reduction temperatures, varying durations at reducing conditions, and varying reducing agent (i.e., H$_2$) flow-rates, to determine the effect of reduction conditions on catalyst conversion. The results are shown in Table 2:

TABLE 2

Catalyst Activation

| Example | Reduction Temp. [° C.] | Reduction Time [h] | H$_2$ Flow-Rate [sccm] | Average Conversion [%] |
|---|---|---|---|---|
| 6 | 400 | 4 | 100 | 82% |
| 7 | 400 | 4 | 500 | 86% |
| 8 | 400 | 8 | 100 | 80% |
| 9 | 400 | 8 | 500 | 90% |

TABLE 2-continued

| | Catalyst Activation | | | |
|---|---|---|---|---|
| Example | Reduction Temp. [° C.] | Reduction Time [h] | $H_2$ Flow-Rate [sccm] | Average Conversion [%] |
| 10 | 500 | 4 | 100 | 69% |
| 11 | 500 | 4 | 500 | 60% |
| 12 | 500 | 8 | 100 | 72% |
| 13 | 500 | 8 | 500 | 79% |

The results of the testing of Examples 6-13 illustrate that those catalysts reduced at temperatures inferior to 500° C. demonstrate improved rates of conversion in comparison to catalysts reduced at temperatures of 500° C. or more. For example, a comparison between Examples 6 and 10, between Examples 7 and 11, between Examples 8 and 12, and between Examples 9 and 13, respectively, each demonstrate that the catalyst reduced at 400° C. exhibits significantly increased conversion in comparison to the otherwise similar catalyst reduced at 500° C. Surprisingly, although these catalysts demonstrate improved conversion rates, the catalysts do not demonstrate a loss in selectivity.

Additionally, the results of the testing of Examples 6-13 also illustrates that reducing in the presence of relatively increased $H_2$ flow rates improves rates of conversion in comparison to catalysts reduced at relatively decreased $H_2$ flow rates.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A process for making a demethylation catalyst, the process comprising reducing a catalyst precursor comprising a transition metal and an inorganic support at a temperature less than 500° C. to produce the demethylation catalyst, wherein the catalyst precursor is reduced in the presence of at least 100 standard cubic centimeters per minute of hydrogen.

2. The process of claim 1, wherein the catalyst precursor is reduced at a temperature less than 450° C.

3. The process of claim 1, wherein the catalyst precursor is reduced at a temperature from 375° C. to 425° C.

4. The process of claim 1, wherein the catalyst precursor is reduced in the presence of a reducing agent.

5. The process of claim 4, wherein the reducing agent is hydrogen.

6. The process of claim 1, wherein the catalyst precursor is reduced in the presence of 100 to 500 standard cubic centimeters per minute of hydrogen.

7. The process of claim 1, wherein the catalyst precursor is reduced in the presence of at least 250 standard cubic centimeters per minute of hydrogen.

8. The process of claim 1, wherein the catalyst precursor is reduced at a temperature less than 450° C. and in the presence of 100 to 500 standard cubic centimeters per minute of hydrogen.

9. The process of claim 1, further comprising impregnating the inorganic support with the transition metal.

10. The process of claim 1, further comprising precipitating the catalyst precursor from a solution including the transition metal, the inorganic support, and a precipitating agent.

11. The process of claim 10, wherein the precipitating agent comprises urea.

12. The process of claim 1, wherein the transition metal comprises iron, cobalt, nickel, ruthenium, rhodium, palladium, osmium, iridium, platinum, or a combination thereof.

13. The process of claim 1, wherein the transition metal comprises nickel.

14. The process of claim 1, wherein the inorganic support comprises an inorganic oxide, talc, a zeolite, a clay, an organically modified clay, or a combination thereof.

15. The process of claim 1, wherein the inorganic support comprises silica, a silicate, an aluminosilicate, alumina, an aluminate, or a combination thereof.

16. The process of claim 1, wherein the demethylation catalyst exhibits an adsorption of hydrogen gas of at least $0.03H_2$:Ni.

17. A demethylation catalyst produced according to the process of claim 1.

18. A process for producing neopentane, the process comprising:
(a) reducing a catalyst precursor comprising a transition metal and an inorganic support at a temperature less than 500° C. to produce a demethylation catalyst; and
(b) contacting a stream including a $C_6$-$C_8$ alkane with hydrogen in the presence of the demethylation catalyst to produce a demethylation product including at least 10 wt % neopentane based on the weight of the demethylation product,
wherein the demethylation catalyst exhibits a conversion rate of the $C_6$-$C_8$ alkane of at least 60%.

19. The process of claim 18, wherein the $C_6$-$C_8$ alkane comprises, neohexane, neoheptane, isooctane, or a combination thereof.

20. The process of claim 18, further comprising separating at least part of the neopentane from the demethylation product.

21. The process of claim 18, wherein contacting the stream with the demethylation catalyst is carried out at a temperature of 200° C. to 500° C.

22. The process of claim 18, wherein contacting the stream with the demethylation catalyst is carried out in the presence of hydrogen at a hydrogen to hydrocarbon molar ratio of 1:1 to 14:1.

23. A composition comprising neopentane produced in accordance with claim 18.

24. A process for producing neopentane, the process comprising:
(a) reducing a catalyst precursor comprising a transition metal and an inorganic support at a temperature less than 500° C. to produce a demethylation catalyst; and
(b) contacting a stream including a $C_6$-$C_8$ alkane with hydrogen in the presence of the demethylation catalyst to produce a demethylation product including at least 10 wt % neopentane based on the weight of the demethylation product, wherein the demethylation product comprises 25 wt % to 50 wt % neopentane based on the weight of the demethylation product and zero wt % to 10 wt % $C_6+$ hydrocarbon components based on the weight of the demethylation product.

\* \* \* \* \*